United States Patent
Lin et al.

(10) Patent No.: US 9,958,406 B1
(45) Date of Patent: May 1, 2018

(54) METHOD OF MEASUREMENT AND ESTIMATION OF THE COEFFICIENT OF THERMAL EXPANSION IN COMPONENTS

(71) Applicant: BLOOM ENERGY CORPORATION, Sunnyvale, CA (US)

(72) Inventors: Cheng-Yu Lin, Sunnyvale, CA (US); Daniel Darga, Pleasanton, CA (US); Michael Groesch, Sunnyvale, CA (US); Harald Herchen, Los Altos, CA (US); Vijay Srivatsan, Sunnyvale, CA (US)

(73) Assignee: BLOOM ENERGY CORPORATION, Sunnyvale, CA (US)

( * ) Notice: Subject to any disclaimer, the term of this patent is extended or adjusted under 35 U.S.C. 154(b) by 668 days.

(21) Appl. No.: 14/559,214

(22) Filed: Dec. 3, 2014

Related U.S. Application Data

(60) Provisional application No. 61/912,931, filed on Dec. 6, 2013.

(51) Int. Cl.
  *G01N 25/16* (2006.01)
  *G01N 27/02* (2006.01)
(52) U.S. Cl.
  CPC .......... *G01N 25/16* (2013.01); *G01N 27/026* (2013.01)
(58) Field of Classification Search
  CPC .... G01N 25/16; G01N 19/04; G01B 9/02021; H01L 21/67248; H01L 2924/351; G01J 5/38

(Continued)

(56) References Cited

U.S. PATENT DOCUMENTS 2,176,784 A  10/1939 Bowden
4,788,627 A * 11/1988 Ehlert ............... H01L 23/3735
                                                174/16.3

(Continued)

FOREIGN PATENT DOCUMENTS

JP    2000-285934 A   10/2000
JP    2007-042406 A    2/2007
WO    2012074972 A2    6/2012

OTHER PUBLICATIONS

U.S. Appl. No. 13/859,829.

(Continued)

*Primary Examiner* — Gail Kaplan Verbitsky
(74) *Attorney, Agent, or Firm* — The Marbury Law Group PLLC

(57) ABSTRACT

Methods and systems for measuring and/or estimating a coefficient of thermal expansion (CTE) of a component of a fuel cell system. A CTE measurement technique includes securing a measurement member over a surface of the component via a seal having a melting point, heating the seal above its melting point of the seal, cooling the component, measurement member and seal to a second temperature below the melting point of the seal, and determining the CTE of the component based on the change in the span of the measurement member after cooling. A fuel cell component characterization technique includes measuring an electrical resistivity (ER), conductivity (EC), resistance or conductance of the component, measuring at least one additional property of the component which, together with ER, EC, resistance or conductance, correlates to the CTE of the component, and sorting the component based on the measurements.

11 Claims, 8 Drawing Sheets

(58) Field of Classification Search
USPC .................. 374/186, 187, 55, 141, 6, 100
See application file for complete search history.

(56) References Cited

U.S. PATENT DOCUMENTS

| | | | |
|---|---|---|---|
| 5,589,772 A | 12/1996 | Kugai | |
| 5,678,566 A * | 10/1997 | Dribbon | A43B 17/00 |
| | | | 600/549 |
| 5,928,803 A * | 7/1999 | Yasuda | A63H 33/22 |
| | | | 374/101 |
| 6,426,161 B1 | 7/2002 | Cisar et al. | |
| 6,599,651 B1 | 7/2003 | Saitou et al. | |
| 7,070,674 B2 * | 7/2006 | Kelley | H01L 41/313 |
| | | | 156/307.7 |
| 7,147,367 B2 * | 12/2006 | Balian | H01L 23/3736 |
| | | | 257/E23.087 |
| 7,422,819 B2 * | 9/2008 | Reisdorf | H01M 8/0282 |
| | | | 429/456 |
| 7,591,584 B2 * | 9/2009 | Beck | G01N 25/16 |
| | | | 374/100 |
| 7,722,246 B1 * | 5/2010 | Carty | G01N 25/16 |
| | | | 252/960 |
| 8,802,331 B2 | 8/2014 | Herchen et al. | |
| 2004/0095127 A1 | 5/2004 | Mohri et al. | |
| 2005/0069017 A1 * | 3/2005 | Arthur | H01M 8/1231 |
| | | | 374/55 |
| 2005/0142431 A1 | 6/2005 | Shimomura et al. | |
| 2006/0127711 A1 | 6/2006 | Kaschmitter et al. | |
| 2008/0199738 A1 | 8/2008 | Perry et al. | |
| 2009/0102599 A1 * | 4/2009 | Scott | H01C 7/02 |
| | | | 338/315 |
| 2010/0297534 A1 * | 11/2010 | Ketcham | H01M 8/0273 |
| | | | 429/508 |
| 2012/0135337 A1 * | 5/2012 | Herchen | G01N 21/95 |
| | | | 429/535 |
| 2017/0089683 A1 * | 3/2017 | Yokoyama | G01N 25/16 |
| 2017/0104233 A1 * | 4/2017 | Armstrong | H01M 8/2484 |

OTHER PUBLICATIONS

U.S. Appl. No. 13/859,892.
U.S. Appl. No. 14/147,785.
Fialkov, A. S. et al., "Diamagnetic susceptibility and Linear Thermal Expansion of Graphitized Carbons," Translated from Poroshkovaya Metallurgiya, No. 8 (32), pp. 87-95, (Aug. 1965).
International Search Report and Written Opinion of the International Searching Authority for PCT/US2011/062328, Nov. 29, 2011, (10 sheets).

* cited by examiner

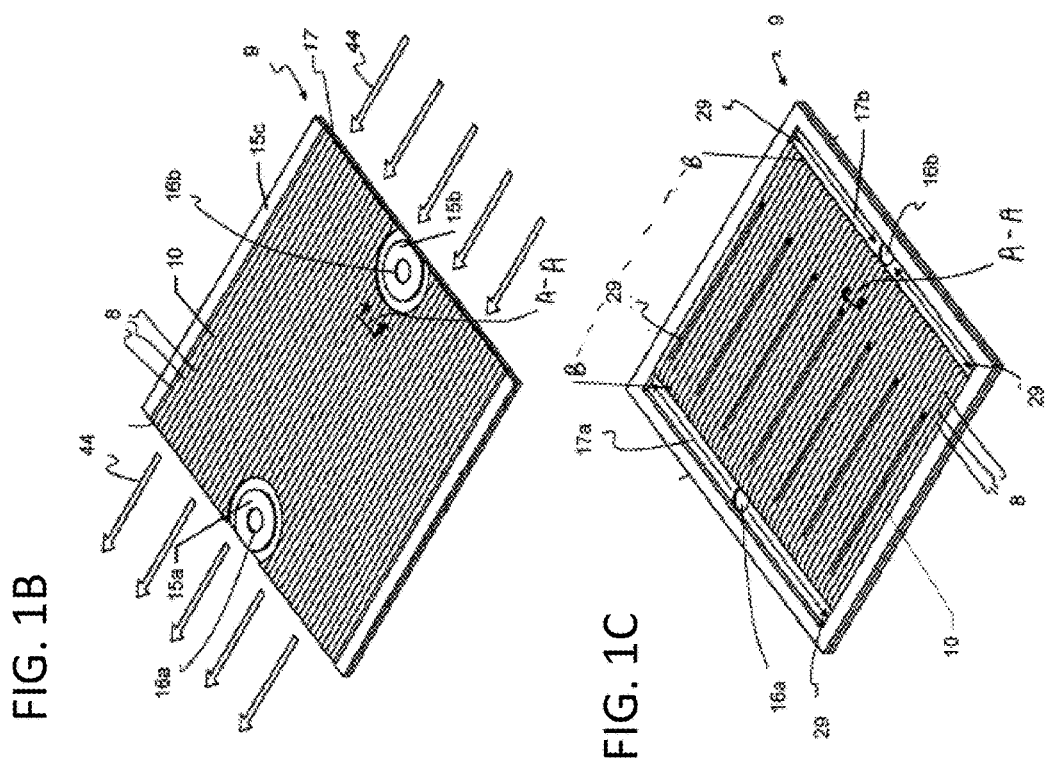

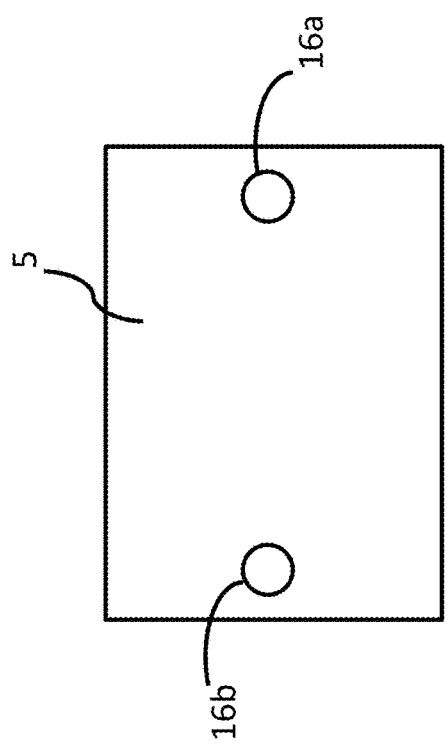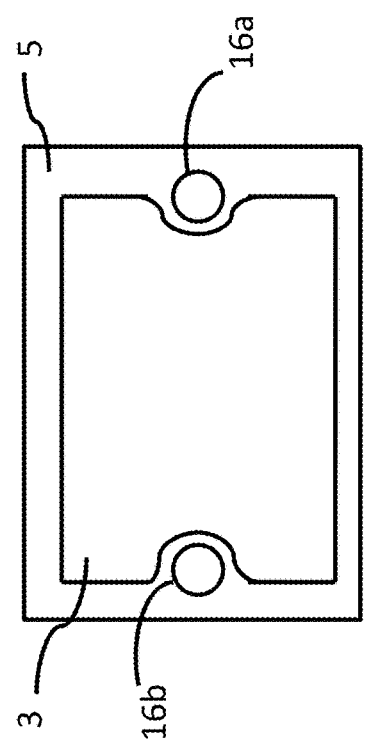
FIG. 2A
FIG. 2B

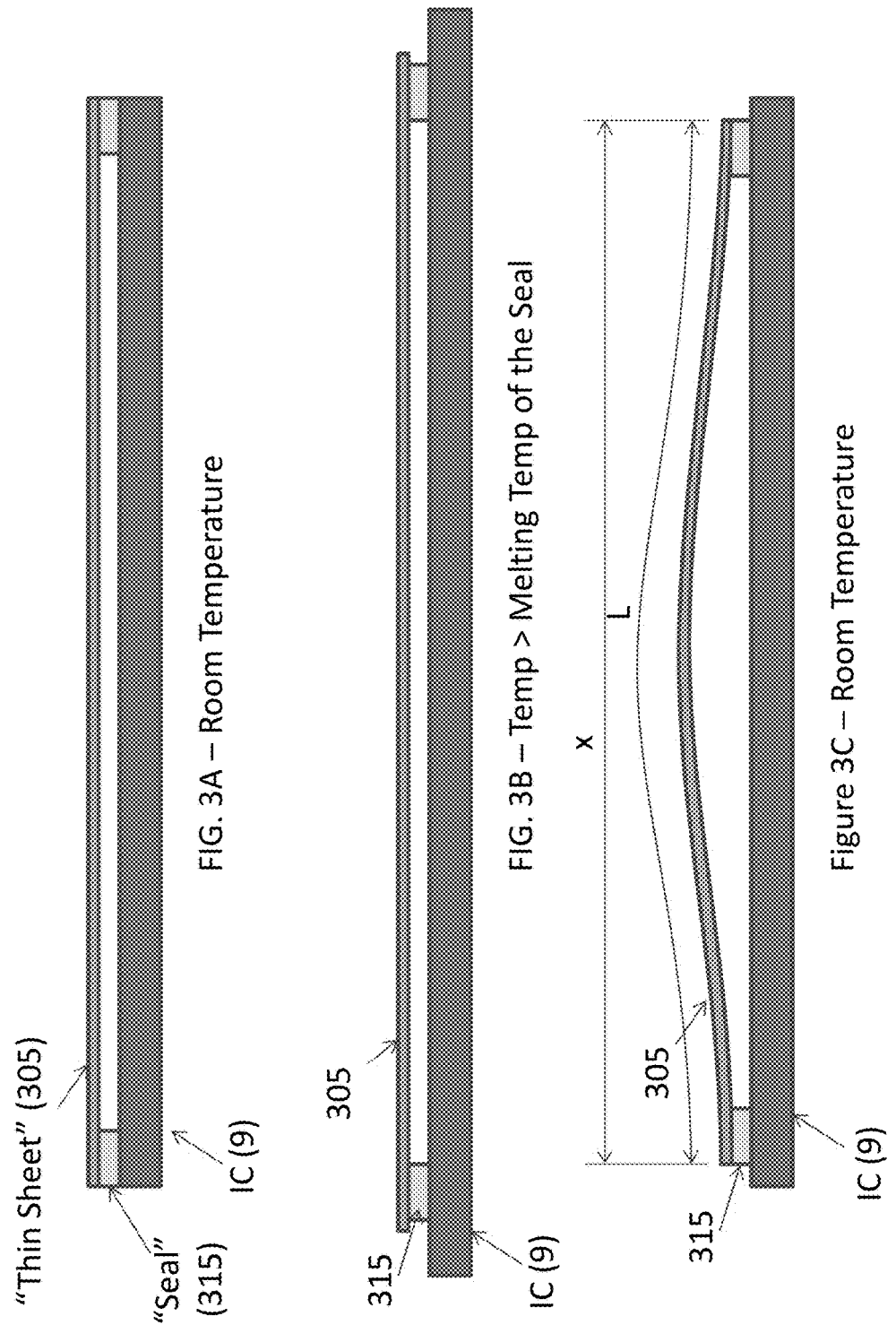

US 9,958,406 B1

METHOD OF MEASUREMENT AND ESTIMATION OF THE COEFFICIENT OF THERMAL EXPANSION IN COMPONENTS

BACKGROUND

In a high temperature fuel cell system, such as a solid oxide fuel cell (SOFC) system, an oxidizing flow is passed through the cathode side of the fuel cell while a fuel flow is passed through the anode side of the fuel cell. The oxidizing flow is typically air, while the fuel flow can be a hydrocarbon fuel, such as methane, natural gas, pentane, ethanol, or methanol. The fuel cell, operating at a typical temperature between 750° C. and 950° C., enables the transport of negatively charged oxygen ions from the cathode flow stream to the anode flow stream, where the ion combines with either free hydrogen or hydrogen in a hydrocarbon molecule to form water vapor and/or with carbon monoxide to form carbon dioxide. The excess electrons from the negatively charged ion are routed back to the cathode side of the fuel cell through an electrical circuit completed between anode and cathode, resulting in an electrical current flow through the circuit.

In order to optimize the operation of SOFCs, the various components of the system, such flow regulating structures including interconnects in the SOFC system, should be precisely manufactured.

SUMMARY

Various embodiments include a method for measuring a coefficient of thermal expansion (CTE) of a component of a fuel cell system that includes securing a measurement member over a surface of the component via a seal having a melting point, heating the component, measurement member and seal to a first temperature above a melting point of the seal, cooling the component, measurement member and seal to a second temperature below the melting point of the seal, and determining the CTE of the component based on a length of the measurement member after cooling.

Further embodiments include methods of characterizing components of a fuel cell system that includes measuring at least one of an electrical resistivity (ER), an electrical conductivity (EC), an electrical resistance and an electrical conductance of a component, measuring at least one additional property of the component which, together with at least one of ER, EC, electrical resistance and electrical conductance correlates to a coefficient of thermal expansion (CTE) of the component, and sorting the component based measuring the at least one of ER, EC, electrical resistance and electrical conductance and the at least one additional property.

In various embodiments, the at least one additional property of the component comprises an X-ray fluorescence (XRF) measurement of the component, an electronic impedance spectroscopy (EIS) measurement of the component, a thickness of the component, a length and width of the component, a mass of the component, a density of the component, a porosity of the component and an amount of nitrides or other contaminants in the component.

Further embodiments include methods of estimating a coefficient of thermal expansion (CTE) of a component of a fuel cell system that includes measuring at least one of an electrical resistivity (ER), an electrical conductivity (EC), an electrical resistance and an electrical conductance of the component, and estimating the CTE of the component based on the measured ER, EC, electrical resistance and electrical conductance.

Further embodiments include systems for performing the above-described measurements of a component of a fuel cell system.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

FIGS. 1B and 1C show, respectively, top and bottom views of an interconnect for a SOFC stack.

FIG. 2A is a plan view of an electrolyte of a fuel cell.

FIG. 2B is a plan view of an electrolyte and an electrode of a fuel cell.

FIGS. 3A-C schematically illustrate a system and method for accurately measuring the CTE of a component of a fuel cell system.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Various embodiments relate to methods of characterizing components of fuel cell systems, such as interconnects for a fuel cell stack.

Figure 1A:
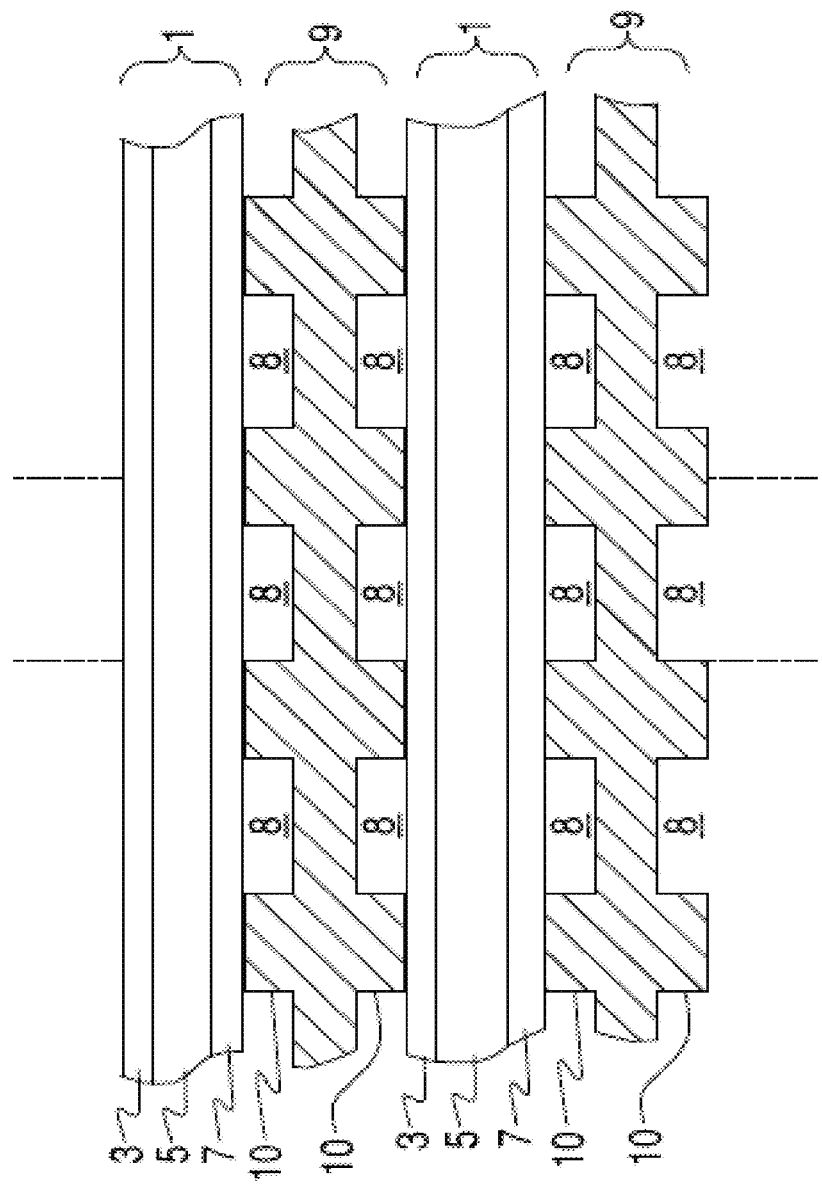
FIG. 1A illustrates a side cross-sectional view of a SOFC stack.

FIG. 1A illustrates a SOFC stack in which each SOFC 1 comprises a cathode electrode 7, a solid oxide electrolyte 5, and an anode electrode 3. Fuel cell stacks are frequently built from a multiplicity of SOFC's 1 in the form of planar elements, tubes, or other geometries. Fuel and air has to be provided to the electrochemically active surface, which can be large.

The gas flow separator 9 (referred to as a gas flow separator plate when part of a planar stack), containing gas flow passages or channels 8 between ribs 10, separates the individual cells in the stack. The gas flow separator plate separates fuel, such as a hydrocarbon fuel, flowing to the fuel electrode (i.e. anode 3) of one cell in the stack from oxidant, such as air, flowing to the air electrode (i.e. cathode 7) of an adjacent cell in the stack. At either end of the stack, there may be an air end plate or fuel end plate (not shown) for providing air or fuel, respectively, to the end electrode.

Frequently, the gas flow separator plate 9 is also used as an interconnect which electrically connects the anode or fuel electrode 3 of one cell to the cathode or air electrode 7 of the adjacent cell. In this case, the gas flow separator plate which functions as an interconnect is made of or contains electrically conductive material. FIG. 1A shows that the lower SOFC 1 is located between two interconnects 9.

FIGS. 1B and 1C show, respectively, top and bottom views of an interconnect 9. The portions of interconnect 9 shown in side cross-section in FIG. 1A are provided along lines A-A in FIGS. 1B and 1C. The interconnect 9 contains gas flow passages or channels 8 between ribs 10. The interconnect 9 in this embodiment includes at least one riser channel 16a for providing fuel to the anode-side of the SOFC 1, as illustrated by arrow 29. The riser channel 16a generally comprises a fuel inlet riser opening or hole that extends through at least one layer of the fuel cells and interconnects in the stack. As illustrated in FIG. 1C, the fuel can flow through the inlet riser channel 16a to the anode-side of each fuel cell. There, the fuel can collect in an inlet plenum 17a (e.g., a groove in the interconnect's surface), then flow over the fuel cell anode 3 through gas flow channels 8 formed in the interconnect 9 to an outlet plenum 17b and then exit through a separate outlet riser channel 16b.

The cathode side, illustrated in FIG. 1B, can include gas flow passages or channels 8 between ribs 10 which direct air flow 44 over the cathode electrode of the fuel cell. Seals 15a, 15b can seal the respective risers 16a, 16b on the cathode-sides of the interconnect and fuel cell to prevent fuel from reaching the cathode electrode of the fuel cell. The seals may have a donut or hollow cylinder shape as shown so that the risers 16a, 16b extend through the hollow middle part of the respective seals 15a, 15b. The seals 15a, 15b can include a elevated top surface for contacting against the flat surface of the adjacent SOFC 1. A peripheral seal 15c can seal the anode-sides of the interconnect and fuel cell to prevent air from reaching the anode electrode of the fuel cell.

An interconnect 9 may be a chromium-based alloy such as 4-6 wt % Fe and 94-96 wt % Cr, with optionally less than about 1 wt % of Y and unavoidable impurities, and may be formed using a powder metallurgy technique. A protective coating (e.g., a lanthanum strontium manganite (LSM) perovskite coating and/or manganese cobalt oxide (MCO) spinel coating) may be formed over at least one surface of the interconnect 9, such as over the cathode-facing surface of the interconnect 9.

FIG. 2A is a plan view of a solid oxide electrolyte 5. The electrolyte 5 may comprise a stabilized zirconia, such as scandia stabilized zirconia (SSZ) or yttria stabilized zirconia (YSZ). Alternatively, the electrolyte 5 may comprise another ionically conductive material, such as a doped ceria. In this embodiment, the electrolyte 5 has a planar geometry, although it will be understood that other geometries, such as a tubular geometry, could be utilized. Riser channel openings 16a, 16b, which in this embodiment comprise circular holes, extend through the electrolyte 5. The riser channels 16a, 16b generally comprise fuel inlet and outlet openings that extend through at least one layer of the fuel cells. The riser channels 16a, 16b can extend through multiple electrolyte layers 5 and interconnects 9 between the electrolyte layers in a fuel cell stack. Fuel can flow through the inlet riser channel 16a to the anode-side of each fuel cell. There, the fuel flows over the fuel cell anode 3 via gas flow channels 8 formed in the gas flow separator/interconnect plate 9, and then exits through separate outlet riser channel 16b.

In FIG. 2B, an anode (e.g., fuel) electrode 3 is shown covering part of a first major surface of the electrolyte 5. A cathode (e.g., air) electrode 7 (not shown) can cover part of the second major surface on the opposite side of the electrolyte 5.

Controlling the coefficient of thermal expansion (CTE) of a SOFC interconnect is important for high volume manufacturing of fuel cell stacks. Variations in interconnect material properties may produce CTE variations large enough to introduce structural issues during the operation of the stack. A SOFC may have an operating temperature between 750° C. and 950° C., and a SOFC may cycle between ambient temperature and its operating temperature multiple times during its operating life. Thus, thermal effects are significant for SOFC performance. The CTE of the interconnects incorporated into the stack may be controlled to ensure the interconnects have relatively uniform thermal properties, both within each individual interconnect and across all the interconnects of the stack. The interconnects may also be designed to be thermally matched to other components of the stack, such as the adjacent (ceramic) fuel cell electrolytes. Thus, measuring the coefficient of thermal expansion (CTE) of interconnects, such as interconnect 9 shown in FIG. 1A-C, may be important for quality control in the manufacturing of an SOFC stack. Standard techniques for measuring CTE using dilatometers have proven insufficiently accurate for quality control, and are also destructive and time consuming. Various embodiments are directed to methods of measuring and/or estimating CTE that overcome some or all of these deficiencies.

FIGS. 3A-C schematically illustrate a system and method for accurately measuring the CTE of a component of a fuel cell system, such as an interconnect 9. The system and method relies on measuring the differential CTE between the interconnect 9 and a second material having a known CTE that is less than the CTE of the interconnect 9. As shown in FIGS. 3A-C, the second material may be a thin sheet 305 of a material that has a lower CTE than the CTE of the interconnect 9. In one embodiment, the thin sheet 305 may be a thin sheet of a ceramic material, such as a stabilized zirconia (e.g., scandia stabilized zirconia (SSZ) or yttria stabilized zirconia (YSZ)) or doped ceria. A seal 315 is provided between the interconnect 9 and the thin sheet 305, as shown in FIG. 3A. The seal 315 may be made of a material having a known melting point, such as glass or glass-ceramic material. As shown in FIG. 3A, the seal 305 may be located along a periphery of a major surface of interconnect 9 (e.g., along all or a portion of at least two opposite edges of the interconnect 9), including along the entire periphery of a major surface of the interconnect 9. The thin sheet 305 may be aligned with the interconnect 9 along at least one dimension, as shown in FIG. 3A.

A method for measuring the CTE of the interconnect includes raising the temperature of the interconnect 9, thin sheet 305 and seal 315 from a first temperature below the melting point of the seal 315 to a second temperature above the melting point of the seal 315. The first temperature may be room temperature (e.g., approx. 20-25° C.) and the second temperature may be greater than 700° C. or more (e.g., 700-1500° C., such as 750-1100° C.). The heating may be done, for example, by placing the interconnect 9, thin sheet 305 and seal 315 assembly into a heating chamber (e.g., a furnace, oven, etc.) and controlling the temperature within the chamber. When the temperature of the assembly exceeds the melting point of the seal 315, the components can move relative to one another and are able to expand independently, as shown in FIG. 3B. As the temperature increases, the interconnect 9, which has a higher CTE than the CTE of the thin sheet 305, expands to a greater degree than the thin sheet, as shown in FIG. 3B.

The method further includes cooling the interconnect 9, thin sheet 305 and seal 315 assembly below the melting point of the seal 315. Cooling the assembly below the seal melting point causes the seal 315 to solidify and bond the thin sheet 305 to the interconnect 9. Thus, as the assembly cools below the seal melting point, the components contract together as a system. The interconnect 9, having a higher CTE than the thin sheet 305, will contract more than the thin sheet 305 during the cool down, which may to room temperature. This causes the thin sheet to "bow," as shown in FIG. 3C.

The differential CTE of the two materials (i.e., material of the interconnect 9 and the material of the thin sheet 305) may then be calculated by measuring the profile of the bowed thin sheet 305. The CTE of the interconnect 9 can be calculated based on the following values, which are either known or may be measured:

the span (e.g., length in a straight line between opposing edges) of the thin sheet 305 (x in FIG. 3C) after cool down. A laser profile scanner or another suitable apparatus may be used for the span measurement;

the line integral (L in FIG. 3C) along the length of the thin sheet after cool down (i.e., the actual length of the thin sheet 305 after cool down);

the temperature differential (dT) between the melting point of the seal 315 and the final temperature of the assembly after cool down (which may be room temperature); and the CTE of the thin sheet, which is known (e.g., from the literature and/or through separate testing).

With these values, the CTE of the interconnect 9 may be calculated using Equation 1:

$$CTE_{IC} = CTE_{Sheet} + (L-x)/(x \cdot dT) \quad \text{Eq. 1}$$

This measurement technique has sources of variation stemming from variations in the melting point of the seal 315 and variations in the known CTE of the thin sheet 305. However, these variations are typically relatively small, and the present method is adequate for accurate measurement of CTE for interconnects 9.

An advantage of the above-described method is that the method may provide extremely accurate measurements of the CTE of an interconnect which has heretofore not been possible using existing techniques. The above-described technique is somewhat time-intensive and costly and may render the interconnect(s) being tested unsuitable for incorporation in a fuel cell stack. Further embodiments include methods and systems for estimating the CTE of interconnects that are rapid, inexpensive and non-destructive. One or more of these methods for CTE estimation may be used to implement quality control, including statistical process control (SPC), of interconnect CTE in fuel cell system fabrication, and in embodiments may be used in conjunction with the above-described CTE measurement technique.

A first method of estimating CTE of a fuel cell system component, such as an interconnect, includes measuring the electrical resistance (or equivalently, measuring the electrical conductance) of the component, and estimating the CTE of all or a portion of the component based on the measured electrical resistance/conductance. Alternatively or in addition, the method may include measuring the electrical resistivity (ER) or conductivity (EC) of the component, and estimating the CTE of all or a portion of the component based on the measured ER or EC. This technique is based on the microstructure of the component, which may include a sintered body comprised of different interdiffused elements having varying resistivity values. For example, the component may be an interconnect formed of a chromium-iron-based alloy formed by powder metallurgy. The measurement of the interconnect's bulk resistivity has been found to be proportional the amount of iron (i.e., total percent of iron in the interconnect) as well as the concentration of iron (i.e., the interdiffusion quality, such as degree of dispersion or clumping of iron particles in the chromium matrix) in the interconnect. The overall resistivity/conductivity of the component may be used to characterize bulk CTE of an interconnect. This technique may also be used to measure the presence of nitrides in a fuel cell system component (e.g., an interconnect), which has been shown to have an influence on the component's CTE.

Figure 4:
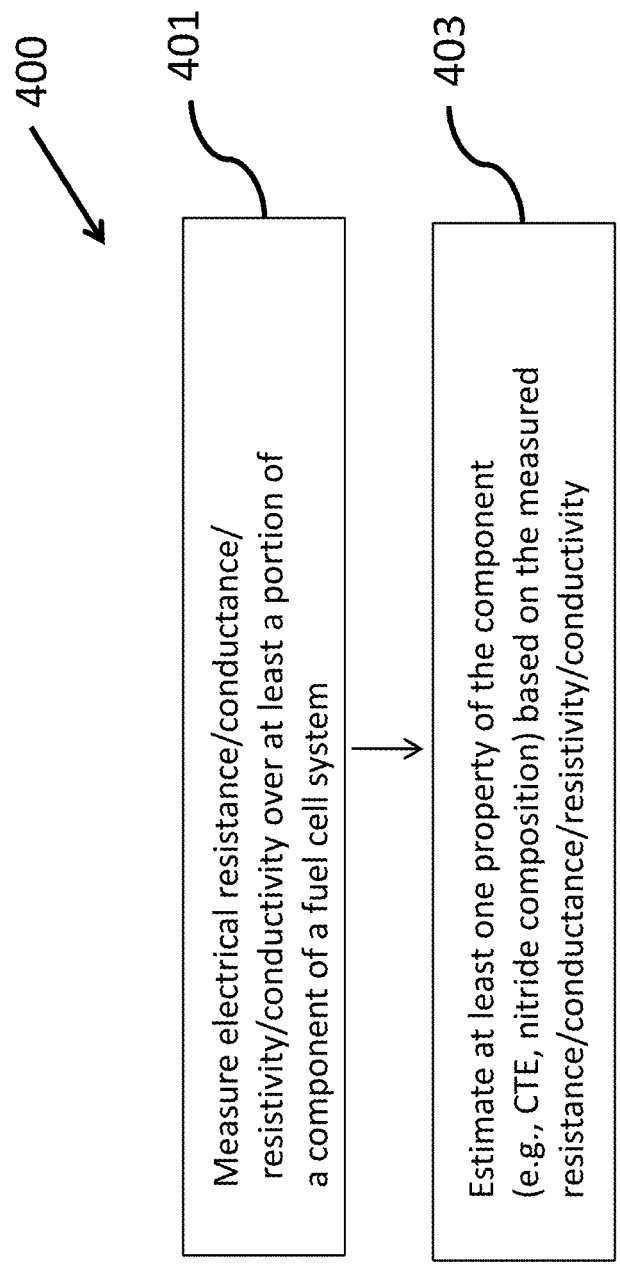
FIG. 4 is a process flow diagram illustrating a method of measuring a property of a component of a fuel cell system by measuring the electrical resistance of the component.
Figure 5:
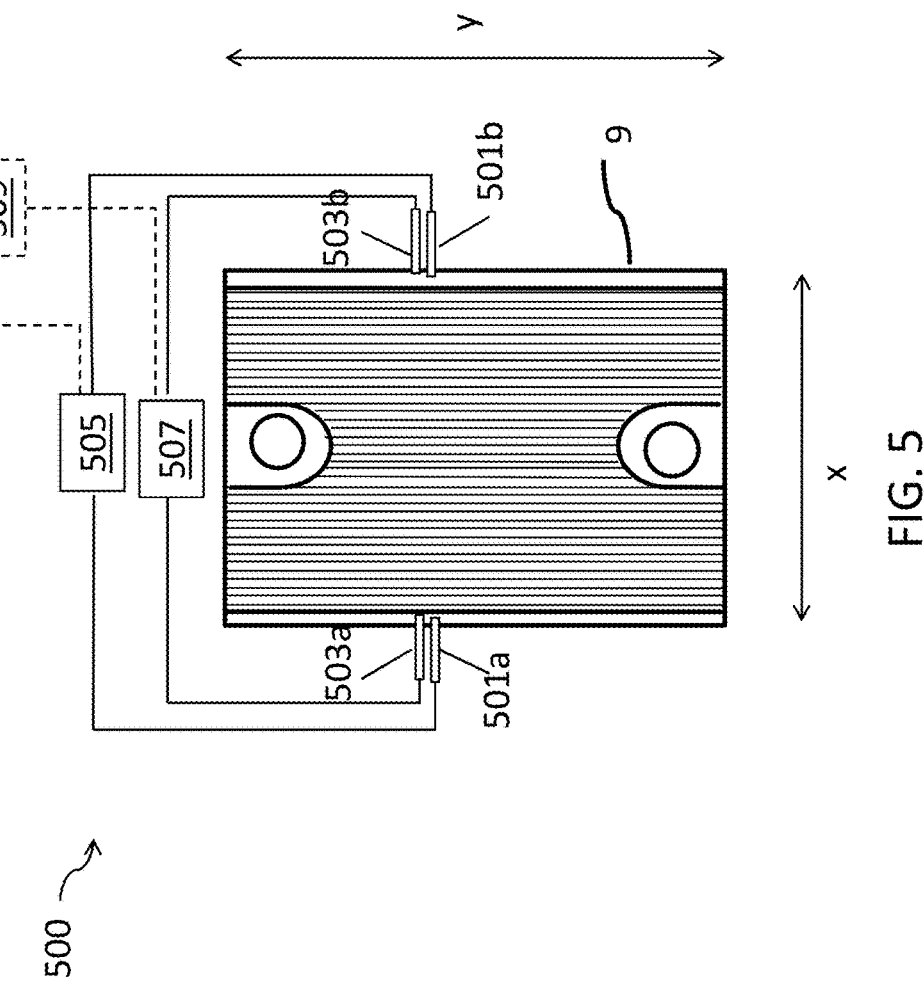
FIG. 5 schematically illustrates an apparatus for measuring the electrical resistance of a component of a fuel cell system.

FIG. 4 is a process flow diagram illustrating a method 400 of measuring a property of a fuel cell system component by measuring an electrical resistivity of the component. FIG. 5 schematically illustrates an apparatus 500 for measuring the electrical resistivity of a fuel cell component, such as an interconnect 9, which may be used in the method 400 of FIG. 4. The interconnect 9 may be made of a chromium-iron (Cr—Fe) alloy produced through a powder metallurgy technique. Blended Cr and Fe elemental powders (and/or pre-alloyed Cr—Fe powders) are pressed in a hydraulic or mechanical press and sintered in a furnace in an inert or reducing (e.g., hydrogen-containing) environment, and may also be heat treated (e.g., oxidized) in air. The CTE and the growth of nitrides in the interconnect are a result of microstructural changes and chemical reactions during the sintering and oxidation steps. It has been shown that the non-ideal CTE variation within the interconnect, as well as between adjacent interconnects negatively affects the yield of fuel cell stack manufacturing. The present method may be used to estimate CTE by measuring the electrical resistance (or its inverse, the electrical conductance) and/or the electrical resistivity or electrical conductivity of the interconnect. The method is non-destructive, inexpensive, and is faster than the cycle time of interconnect production, and thus can be used as an in-line measurement and characterization tool.

The method 400 may include measuring at least one of electrical resistance, electrical conductance, electrical resistivity and electrical conductivity over at least a portion of a component of a fuel cell system as shown in block 401. In one embodiment, electrical resistance may be measured by providing a known current through a portion of the interconnect and measuring the associated voltage drop over one or more portions of the interconnect. This may yield the resistance, R, of the interconnect which may be used to calculate the resistivity, $\rho$ (e.g., $\rho = R^*(l/A)$, where l is the length of the current path and A is the cross-sectional area of the current path). The conductivity, $\sigma$ is the inverse of the resistivity, or $\sigma = 1/\rho$. The electrical conductance, G, is the inverse of resistance, or $G = 1/R$. FIG. 5 illustrates an embodiment apparatus 500 for measuring the electrical resistivity of an interconnect 9. A pair or electrical connectors 501a, 501b connected to a current source 505 are contacted against the interconnect 9. The current source 505 delivers a known current through the interconnect 9 via the connectors. A pair of probes 503a, 503b connected to a volt meter 507 are used to measure the voltage drop across the interconnect 9. Based on the measured voltage drop and the known input current, the resistance may be determined. One or more sets of electrical connectors 501a, 501b and measurement probes 503a, 503b may be contacted at various points on the interconnect 9 to map the resistance or resistivity over different portions of the interconnect 9. In embodiments, the probes 503a, 503b may measure from corner to corner of the interconnect 9 in order to obtain a uniform measurement of the part.

The method 400 may also include estimating at least one property of the component, such as its CTE and/or nitride composition, based on the measured resistance/conductance or resistivity/conductivity values as shown in block 403. Applicants have discovered that the CTE of an interconnect is affected by the diffusion of iron into chromium during the interconnect manufacturing process (e.g., during the sintering step). The CTE of a well-diffused (i.e., well-alloyed, e.g., where iron is dispersed fairly evenly throughout the chromium matrix) interconnect is higher than that of an un-diffused or partially diffused interconnect (e.g., where iron or iron rich particles/regions are located throughout the chromium matrix). The electrical conductivity of chromium is also different from the conductivity of iron. Therefore, interconnects with un-diffused or partially diffused iron into the chromium matrix will have different electrical conductivity (and resistivity) compared to an interconnect with fully diffused iron into the chromium matrix. The method 400 may make use of this physical property to use electrical resistance/conductance/resistivity/conductivity as an estimate of the CTE of the interconnect. The resistance/conductance or resistivity/conductivity may be measured as described above, with pairs of current input and output connectors 501a, 501b, with voltage probes 503a, 503b strategically distributed on a surface of the interconnect, which may be an un-coated surface, meaning no protective coating (such as a lanthanum strontium manganite (LSM) perovskite coating and/or an manganese cobalt oxide (MCO) spinel coating) is present. The finite conductivity of the part leads to a voltage distribution across the part. The voltage difference between pairs of probes 503a, 503b at various locations on the part may be measured and compared to well-characterized standards. The current source 505 may provide direct current since this may flow through the bulk of the part. Measurement of voltage differences across multiple probes may give a measurement of the resistance/conductance or resistivity/conductivity of the part and therefore provide the means to estimate the CTE.

Applicants have also discovered that nitrides (e.g., chromium and/or iron nitride regions or particles) may grow along grain boundaries within the microstructure of the interconnect. Nitrides have significantly lower conductivity compared to pure chromium, iron or chromium-iron alloy. Due to the widespread nature of nitride growth, electrical conductivity is reduced in interconnects that have significant nitride growth. The apparatus 500 as described above in connection with FIG. 5 may be used to map the presence and concentration of nitrides within the interconnect.

In cases where it may be necessary to distinguish between nitrides and Fe/Cr interdiffusion differences for regions in the bulk of the interconnect, electronic impedance spectroscopy (EIS) is sensitive to the interparticle nitrides, especially due to the capacitance thereof. By contrasting an EIS measurement with DC resistance/conductance or resistivity/conductivity measurements (e.g., very low frequency), the contribution of the two may be separated. This may be useful for diagnostic purposes, as well as for CTE matching in an in-line tool.

In cases where it is desired to detect surface nitrides, excitation of the interconnect at MHz or higher frequencies allows the excitation to be constrained to the surface of the interconnect due to the skin effect. This method affords an additional method to detect residual surface nitrides. These surface nitrides are present in some cases, and may affect the ability of a protective coating (e.g., LSM and/or MCO spinel) to stick to the interconnect surface. Detecting these nitrides may be accomplished using the method described above an/or by optical techniques.

Measuring the electrical resistance/conductance or resistivity/conductivity of fuel cell system components, such as interconnects, may provide a useful first order analysis of the CTE of the components. A resistance/conductance or resistivity/conductivity measurement of a fuel cell system component, such as an interconnect, may be compared to the equivalent measurement of similar components for which the CTE is known (e.g., determined using the method described above in connection with FIGS. 3A-C) to provide a rough approximation of the CTE. In some embodiments, the resistance/conductance or resistivity/conductivity measurement may not necessarily be used to calculate the actual magnitude of the CTE, but may be used to estimate variations in CTE between a plurality of components (e.g., from a particular batch or production run), to identify statistical outliers within a group of components and/or to sort components (e.g., interconnects) based on similar CTE. The sorting of components based on detected resistance/conductance or resistivity/conductivity measurements may be performed using a logic device (e.g., a computer) 509, as shown in FIG. 5.

Figure 6:
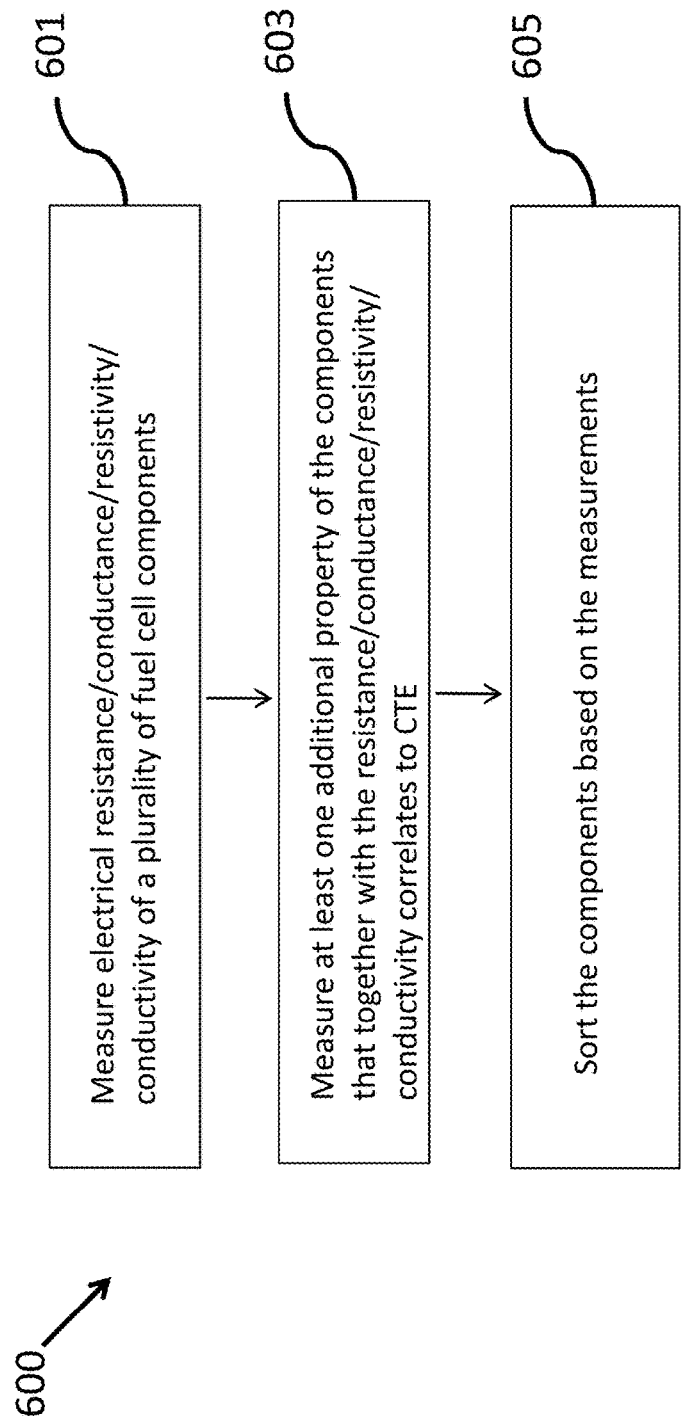
FIG. 6 is a process flow diagram illustrating a method of characterizing components of a fuel cell based on electrical resistance, conductance, resistivity and/or conductivity and at least one other property that together with electrical resistance, conductance, resistivity and/or conductivity correlates to CTE of the component.

In one embodiment, shown in the process flow diagram of FIG. 6, a method 600 of characterizing components of a fuel cell system includes measuring the electrical resistance/conductance or resistivity/conductivity of a plurality of components (block 601), measuring at least one other property of the components which together with resistance/conductance or resistivity/conductivity correlates to CTE of the components (block 603), and sorting the components based on the measurements (block 605).

The at least other property of the component may be a property of the component that influences the electrical resistance/conductance or resistivity/conductivity measurement, such as the thickness of the component (e.g., thickness between two major surfaces of an interconnect), the x and y dimensions of the component (e.g., the length and width dimensions of an interconnect, as shown in FIG. 5), the amount of nitrides and/or other contaminants that affect electrical resistance/conductance in the component, porosity of the component, mass of the component, and/or density of the component. The at least one other property of the component may be obtained using a separate measurement technique, such as an x-fluorescence (XRF) measurement and/or an electronic impedance spectroscopy (EIS) measurement.

The at least one additional property of the component may be combined with the resistance/conductance or resistivity/conductivity measurement to provide a refined, or second order CTE approximation. In embodiments, the components may be sorted using a "look up table" of stored values of electrical resistance/conductance or resistivity/conductivity and the at least one other property which together with the electrical resistance/conductance or resistivity/conductivity correlates to CTE. For example, a lookup table may define a particular range of resistance/conductance values as corresponding to an acceptable CTE when the component also falls within a particular thickness range. The range of acceptable resistance/conductance values may be generally lower for thicker components (e.g., end plates) than for thinner components (e.g., interconnects), since the measured resistance/conductance is influenced by the thickness of the component. In other embodiments, a multivariable analysis may be performed based on the measured resistance/conductance and the at least one additional property (e.g., a least squares fit regression analysis). The components may be sorted based on the analysis (e.g., rejected/accepted for use in a fuel cell stack). The analysis may be performed by a logic device (e.g., a computer) 509, as schematically illustrated in FIG. 5. In various embodiments, the components may be sorted without actually determining the CTE of the components. For example, components may be sorted based on comparing measured resistance or conductance values to a lookup table or predetermined resistance or conductance range(s).

X-ray fluorescence (XRF) is a well-established method which may be used to directly measure the composition of a surface being inspected, and may be used to measure the percent composition of iron on a surface of a chromium-iron-based interconnect. As discussed above, the CTE of a chromium-iron based interconnect is related to its percent iron composition (i.e., the higher the iron concentration, the higher the CTE). A measurement of the percent iron composition on a surface of the interconnect using XRF may be used to estimate the total iron concentration of the interconnect. The estimate may also be influenced by various characteristics of the interconnect, such as the surface preparation, the evaporation and recondensation of chromium, and the chromium diffusion into iron particles, which is generally from below the surface only.

A method for measuring the magnetic response (MR) of a fuel cell system component, such as an interconnect, is described in commonly-owned U.S. Patent Application Publication No. 2012/0135337 to Herchen et al., the entire contents of which are incorporated herein by reference. A magnetic attraction may be observed between an interconnect and a magnet due to the iron content in the interconnect. This attraction is proportional to the quantity of discrete iron particles or magnetic domains in the interconnect. Furthermore, it has been shown that as the fraction of discrete iron particles drops (i.e., as the interdiffusion of Fe and Cr increases through sintering), so too does the interconnect's ability to attract a magnet. A magnetic response (MR) measurement may include placing a magnet on a scale with an iron-based surface such that the magnet is attracted to the scale. A fixture is positioned above the scale such that an interconnect may be located close to and above the magnet. The magnetic attraction between the interconnect and the magnet pulls the magnet up, and the scale measures the magnitude of the attraction as a negative force. With this measurement technique, one may characterize the nature of the iron content within the interconnect. If the interconnect contains a larger percentage of iron, there will be a larger attraction. Also, the more the interconnect is sintered (e.g., the greater the degree of interdiffusion between Cr and Fe), the lower the magnetic attraction between the interconnect and the magnet will be. Thus, for a constant amount of iron, a lower MR measurement indicates a higher CTE (less pure Fe available due to more diffusion). Conversely, for a constant amount of sintering, a higher MR measurement indicates a higher CTE (more pure Fe available due to increased Fe % in the base material). The MR measurement may be influenced by various characteristics of the interconnect, such as thickness, distance to the magnet, nitride levels, shape of the magnetic field of the magnet, and error from other ferromagnetic material contamination (coating, nitrides, etc.). MR may provide a good indication of process stability as it relates to CTE of a fuel cell system component.

XRF may be used to estimate total iron content, the influence of this factor on the ER measurement may be used to provide a more accurate CTE estimation.

Figure 7:
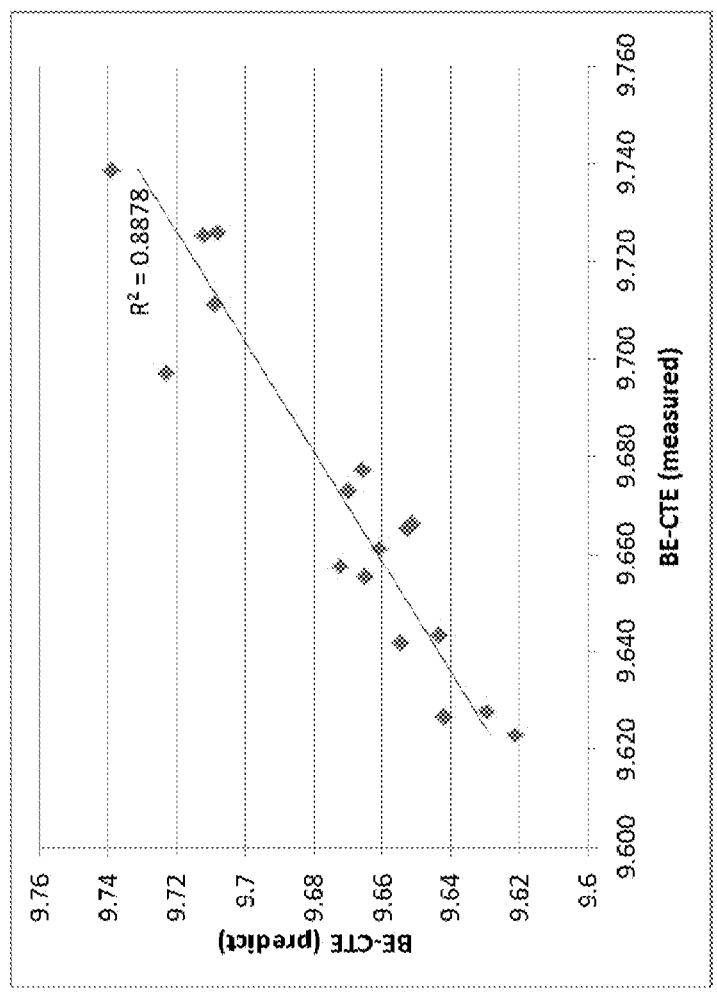
FIG. 7 is a typical plot of predicted CTE using multivariable regression analysis vs. measured CTE using the technique of FIGS. 3A-C.

In some embodiments, the method of estimating CTE based on electrical resistance/conductance or resistivity/conductivity and at least one other property that together with resistance/conductance or resistivity/conductivity correlates to CTE may be combined with an accurate method of measuring the CTE of a fuel cell system component (e.g., an interconnect), such as the method described above in connection with FIGS. 3A-C. A formula may be derived for predicting the CTE of the component based on a measurement of resistance/conductance or resistivity/conductivity and at least one other property of the component that together with resistance/conductance or resistivity/conductivity correlates to CTE of the component. In one non-limiting example illustrating the effect of variations in iron content and sintering quality of interconnects, a linear regression of CTE measured vs. predicted using the variables of ER, mass and thickness resulted in a correlation with an $R^2=0.89$. The results are shown in FIG. 7.

The ability to estimate CTE by measuring characteristics such as electrical resistance/conductance, resistivity/conductivity, XRF, mass and thickness may greatly enhance quality control in the manufacturing of fuel cell systems, particularly as it relates to interconnect variations. Measurements of electrical resistance/conductance, resistivity/conductivity, mass, x-y dimensions and XRF are all non-destructive, quick, and inexpensive, and do not require the use of proprietary materials. This may enable true statistical process control (SPC) of interconnect CTE during production. In one embodiment, measurements from a plurality of fuel cell system components (e.g., batches of interconnects) may be used to establish control limits. When a component or batch of components fails these control limits, the component(s) may be put on hold for further investigation, such as by measuring select components using the technique described above in connection with FIGS. 3A-C. This may help identify components and/or groups of components that would produce low stack yield due to CTE mismatches before the defective components are incorporated into the fuel cell stacks.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A method for measuring a coefficient of thermal expansion (CTE) of a component of a fuel cell system, comprising:
 securing a measurement member over a surface of the component via a seal having a melting point, the measurement member being secured to a first portion of the seal and a second portion of the seal;
 heating the component, measurement member and seal to a first temperature above the melting point of the seal;
 cooling the component, measurement member and seal to a second temperature below the melting point of the seal;
 measuring a length of the measurement member at the second temperature;
 measuring a distance between the first portion of the seal and the second portion of the seal;
 calculating the difference in temperature between the melting point of the seal and the second temperature; and
 determining the CTE of the component based on the length of the measurement member after cooling, a distance between the first and second portions of the seal and the difference in temperature between the melting point of the seal and the second temperature.

2. The method of claim 1, wherein the measurement member comprises a sheet of a material having a known CTE, wherein the known CTE is less than the CTE of the component.

3. The method of claim 1, wherein at least one of:
 (i) the component comprises an interconnect for a fuel cell stack; and
 (ii) the seal comprises a glass or glass-ceramic seal.

4. The method of claim 3, wherein the component comprises an interconnect, and the interconnect comprises 95-96 wt % chromium and 4-6 wt % iron.

5. The method of claim 1, wherein the component and the measurement member expand independently of each other at a temperature above the melting point of the seal and contract together at a temperature below the melting point of the seal.

6. The method of claim 5, wherein the contraction of the component and the measurement member causes the measurement member to assume a bowed profile, and the length of the measurement member comprises a line integral of the bowed profile, wherein the line integral is measured along a length of the measurement member after cooling the component, measurement member and seal.

7. The method of claim 6, wherein the CTE of the component is determined based on the line integral of the bowed profile, the distance between the first and second portions of the seal, the known CTE of the measurement member, and a temperature differential between the melting point of the seal and the second temperature of the component, seal and measurement member after cooling using a formula:

$$CTE_{IC} = CTE_{MM} + (L-x)/(x \cdot dT),$$

where $CTE_{IC}$ is the CTE of the component, $CTE_{MM}$ is the known CTE of the measurement member, L is the line integral of the bowed profile, x is the distance between the first and second portions of the seal, and dT is the temperature differential between the melting point of the seal and the second temperature of the component, seal and measurement member.

8. An apparatus for measuring a coefficient of thermal expansion (CTE) of a component of a fuel cell system comprising a measurement member and a seal for securing the measurement member over a surface of the component, wherein the apparatus measures the CTE of the component in accordance with the method of claim 1.

9. The method of claim 1, further comprising determining the melting point of the seal by relative movement between the component and the measurement member.

10. The method of claim 1, wherein the melting point of the seal is known melting point.

11. The method of claim 7, wherein the second temperature is room temperature.

* * * * *